US009340782B2

(12) United States Patent
Olson et al.

(10) Patent No.: US 9,340,782 B2
(45) Date of Patent: May 17, 2016

(54) ANTIMIR-451 FOR THE TREATMENT OF POLYCYTHEMIAS

(75) Inventors: Eric N. Olson, Dallas, TX (US); David Patrick, Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 367 days.

(21) Appl. No.: 13/574,398

(22) PCT Filed: Jan. 20, 2011

(86) PCT No.: PCT/US2011/021886
§ 371 (c)(1),
(2), (4) Date: Sep. 11, 2013

(87) PCT Pub. No.: WO2012/148373
PCT Pub. Date: Nov. 1, 2012

(65) Prior Publication Data
US 2014/0011859 A1 Jan. 9, 2014

Related U.S. Application Data

(60) Provisional application No. 61/296,783, filed on Jan. 20, 2010, provisional application No. 61/282,546, filed on Feb. 26, 2010.

(51) Int. Cl.
*A61K 48/00* (2006.01)
*C12N 15/113* (2010.01)

(52) U.S. Cl.
CPC ........ *C12N 15/113* (2013.01); *C12N 2310/113* (2013.01); *C12N 2310/315* (2013.01); *C12N 2310/3231* (2013.01); *C12N 2310/346* (2013.01)

(58) Field of Classification Search
None
See application file for complete search history.

(56) References Cited

U.S. PATENT DOCUMENTS

| 8,247,543 B2* | 8/2012 | Tuschl et al. ................. 536/24.5 |
| 2009/0281167 A1 | 11/2009 | Shen et al. |
| 2009/0326051 A1 | 12/2009 | Corey et al. |

FOREIGN PATENT DOCUMENTS

| JP | 2008-539699 | 11/2008 |
| WO | WO 2007/112754 A2 | 10/2007 |

OTHER PUBLICATIONS

"International Search Report," 4 pages, PCT Appl. No. PCT/US11/21886 (mailed Apr. 13, 2011).
"Written Opinion of the International Searching Authority," 8 pages, PCT Appl. No. PCT/US11/21886 (mailed Apr. 13, 2011).
Bruchova et al., "The Regulated Expression of miRNAs in Normal and Polycythemia Vera Erythropoiesis," Exp. Hematol. 35:1657-1667 (2007).
Dickins et al., "Probing tumor phenotypes using stable and regulated synthetic microRNA precursors," Nat. Genet. 37(11):1289-1295 (2005).
Dore et al., "A GATA-1-regulated microRNA locus essential for erythropoiesis," Proc. Natl. Acad. Sci. USA 105:3333-3338 (2008).
Garzon et al., "MicroRNA fingerprints during human megakaryocytopoiesis," Proc. Natl. Acad. Sci. USA 103(13):5078-5083 (2006).
Georgantas III et al., "CD34+ hematopoietic stem-progenitor cell microRNA expression and function: A circuit diagram of differentiation control," Proc. Natl. Acad. Sci. USA 104(8):2750-2755 (2007).
Nand et al., "Leukemic transformation in polycythemia vera: analysis of risk factors," Am. J. Hematol. 34(1):32-36 (1990) PubMed Abstract.
Pase et al., "mir-451 regulates zebrafish erythroid maturation in vivo via its target gata2," Blood 113(8):1794-1804 (2009).
Zhan et al. "MicroRNA expression dynamics during murine and human erythroid differentiation," Exp. Hematol. 35(7):1015-1025 (2007).
Bruchova et al., "Dysregulated expression of miRNAs in polycythemia vera erythroid progenitors," *Blood*, ASH Annual Meeting Abstracts, 108: Abstract 3613, 2006.
Office Action issued in Japanese Application No. 2013-512611, mailed Jan. 9, 2015, and English language translation thereof.
Bruchova et al., "Erythropoiesis in polycythemia vera is hyper-proliferative and has accelerated maturation," *Blood Cells*, Molecules, and Diseases, 43:81-87, 2009.
Office Action and Search Report issued in Chinese Application No. 201180014268.5, mailed Sep. 19, 2014 (English language translation thereof).
Extended European Search Report issued in European Application No. 11856627.2, mailed Dec. 15, 2014.
Masaki et al., "Expression patterns of microRNAs 155 and 451 during normal human erythropoiesis," *Biochemical and Biophysical Research Communications*, 364:509-514, 2007.
Merkerova et al., "Differential expression of microRNAs in hematopoietic cell lineages," *European Journal of Haematology*, 81:304-310, 2008.
Nagata et al., "Differential microRNA expression between bone marrow side population cells and hepatocytes in adult mice," *International Journal of Molecular Medicine*, 24:35-43, 2009.
Papapetrou et al., "A genetic strategy for single and combinatorial analysis of miRNA function in mammalian hematopoietic stem cells," *Stem Cells*, 28:287-296, 2010.

(Continued)

*Primary Examiner* — Kimberly Chong
(74) *Attorney, Agent, or Firm* — Parker Highlander PLLC

(57) ABSTRACT

The present invention provides methods of treating diseases and disorders associated with aberrant erythropoiesis. Specifically, the present invention provides a method for treating polycythemia in a subject by administering an inhibitor of miR-451. Methods of increasing red blood cell count and treating anemia in a subject by administering miR-451 mimetics are also disclosed.

9 Claims, 13 Drawing Sheets

(56) References Cited

OTHER PUBLICATIONS

Pase et al., "miR-451 regulates zebrafish erythroid maturation in vivo via its target gata2," Blood, 113:1794-1804, 2009 and Supplemental Materials.

Shizuki et al., "Expression analysis of microRNAs in erythropoiesis," Abstract only, 56(12):1086-1092, 2008.

Zhan and Song, "MicroRNA and erythroid differentiation," *Current Perspectives in microRNAs (miRNA)*, Chapter 6, pp. 97-117, 2008.

\* cited by examiner

FIGURE 6
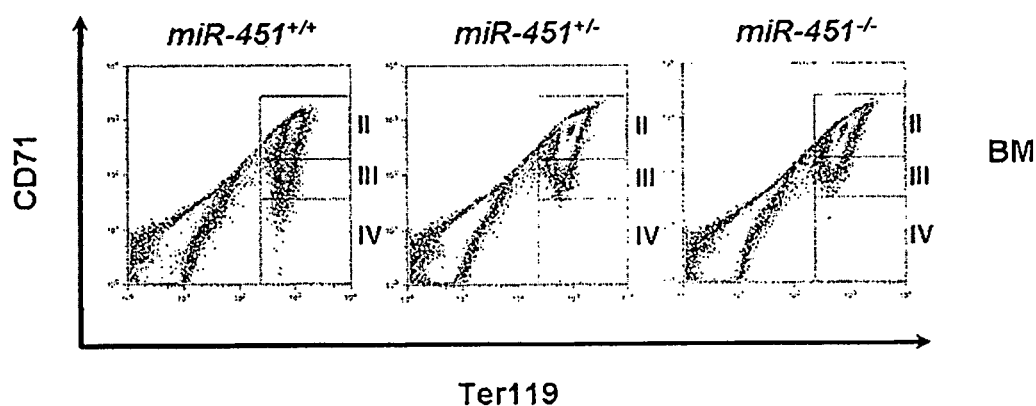
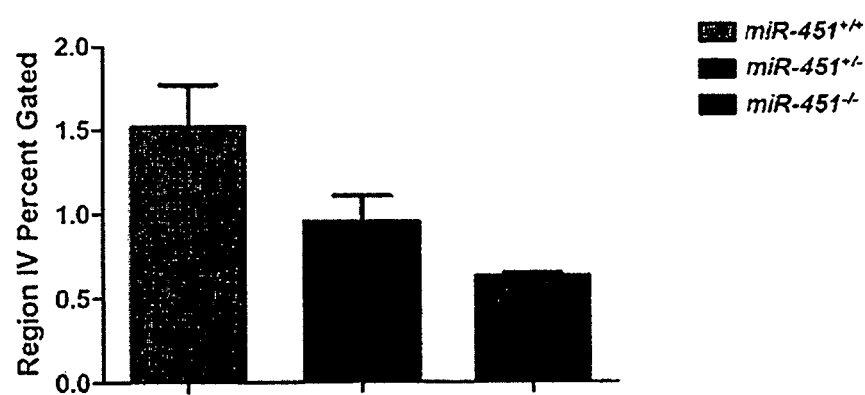

FIGURE 8
A
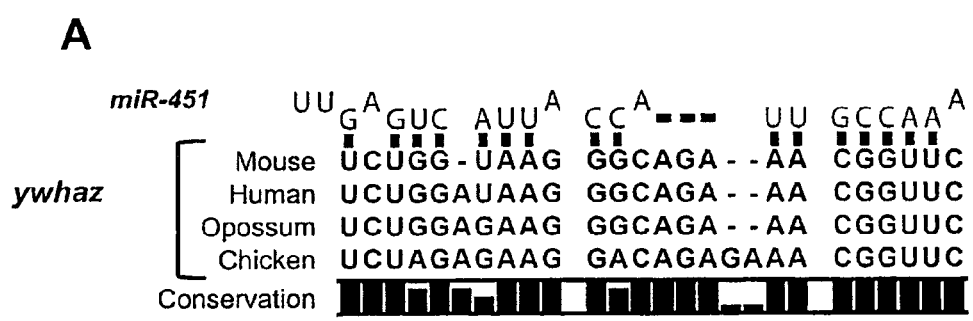
B
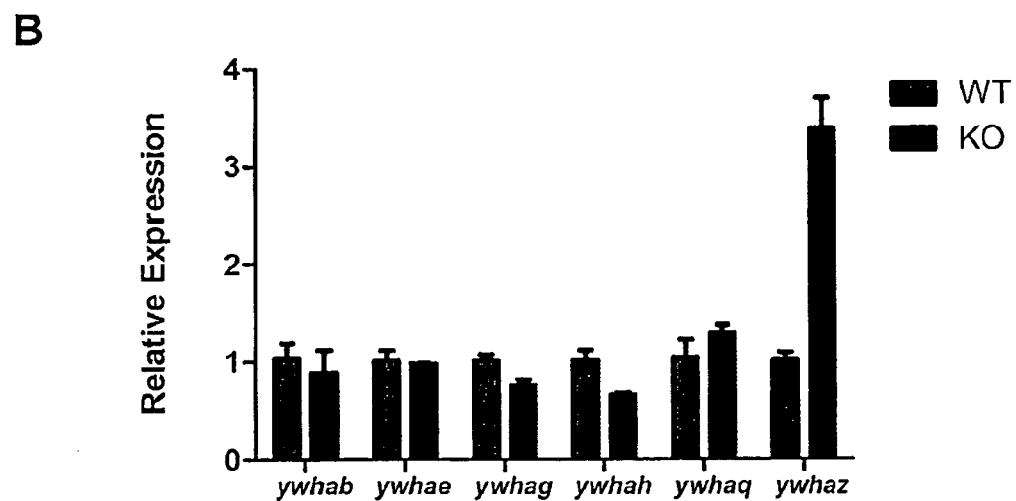

ANTIMIR-451 FOR THE TREATMENT OF POLYCYTHEMIAS

CROSS-REFERENCE TO RELATED APPLICATIONS

This application is a U.S. national stage application of International Application No. PCT/US2011/21886, which was filed on Jan. 20, 2011 and claims the benefit of U.S. Provisional Application No. 61/296,783, filed Jan. 20, 2010, and U.S. Provisional Application No. 61/282,546, filed Feb. 26, 2010, each of which is herein incorporated by reference in its entirety.

STATEMENT OF GOVERNMENT SUPPORT

This invention was made with government support under Grant Number HL093039 awarded by the National Institute of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_021_US_SeqList_ST25.txt, date recorded: Jun. 13, 2014, file size 9 kilobytes).

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_021_01WO_SeqList_ST25.txt, date recorded: Jan. 20, 2011, file size 6 kilobytes).

FIELD OF THE INVENTION

The present invention relates to the treatment of disorders and diseases associated with aberrant erythropoiesis by regulating the activity or expression of microRNAs (miRNAs). In particular, the invention relates to treating polycythemia or anemia by regulating the expression of miR-451.

BACKGROUND OF THE INVENTION

Polycythemia, or an inappropriate increase in red blood cell mass, may be either congenital or acquired. Primary polycythemia, also known as polycythemia vera (PV), is an acquired disease that derives from the clonal expansion of myeloid progenitor cells that have acquired the JAK2-V617F mutation. This mutation, observed in 95% of PV cases, induces excessive maturation of erythrocyte progenitors resulting in excess circulating mature erythrocytes. Approximately 2 per 100,000 people have PV, with the prevalence being higher in men than women. Significant morbidity and mortality due directly to increased red cell mass is observed including cerebrovascular events, myocardial infarction, deep venous thrombosis, and pulmonary embolism. Median survival from the time of diagnosis is approximately 13 years, with more than 40% of deaths attributed to thrombotic events. Currently, the primary therapy for this disease is control of red cell mass by phlebotomy. For the appropriate treatment of PV, therapeutic compounds must be developed to directly lower red cell mass without significant toxicity.

Anemia, which is a decrease in the normal number of red blood cells or a decrease in the normal level of hemoglobin in the blood, is the most common disorder of the blood and can be caused by various factors, including excessive blood loss (e.g., hemorrhage), excessive destruction of blood cells (e.g., hemolysis), and deficient red blood cell production (e.g., defective erythropoiesis). Current treatments for anemia are often dependent on the underlying cause and include iron supplementation, exogenous erythropoietin, and blood transfusions. In particular, aplastic anemia results from the inability of the bone marrow to produce a sufficient amount of blood cells. Aplastic anemia typically does not respond to conventional anti-anemia treatments and can require bone marrow transplants to ameliorate the condition. Thus, there is a continuing need for additional treatments, particularly those that act to increase blood cell production, for anemia.

MiRNAs have recently been implicated in a number of biological processes including regulation of developmental timing, apoptosis, fat metabolism, and hematopoietic cell differentiation among others. MiRNAs are small, non-protein coding RNAs of about 18 to about 25 nucleotides in length that are derived from individual miRNA genes, from introns of protein coding genes, or from poly-cistronic transcripts that often encode multiple, closely related miRNAs. See review by Carrington et al. (*Science*, Vol. 301(5631):336-338, 2003). MiRNAs act as repressors of target mRNAs by promoting their degradation, when their sequences are perfectly complementary, or by inhibiting translation, when their sequences contain mismatches. Many miRNAs are tissue specific, allowing them to regulate ubiquitously expressed genes in a tissue specific manner. Due to these properties, it is likely that the regulation of miRNAs could therapeutically impact complex disease states in a tissue specific manner.

SUMMARY OF THE INVENTION

The present invention is based, in part, on the discovery that miR-451 is required for normal erythropoiesis, and reduction in the amount of miR-451 expression results in a significant reduction of mature erythrocytes. Thus, modulation of miR-451 expression provides a therapeutic approach to treating disorders and diseases associated with aberrant erythropoiesis, such as polycythemia and anemia. Accordingly, in one embodiment, the present invention provides a method for treating polycythemia in a subject in need thereof, including a human, by administering an inhibitor of miR-451 to the subject. In certain embodiments, miR-451 inhibitors are modified or unmodified antisense oligonucleotides comprising a sequence that is at least partially complementary to all or a portion of a mature miR-451 sequence. In some embodiments, a subject's red blood cell count is reduced following administration of a miR-451 inhibitor. The subject may be diagnosed with, suffering from, or at risk of developing polycythemia vera, primary familial and congenital polycythemia, or a disease associated with polycythemia.

The present invention also includes a method of increasing red blood cell count in a subject. In one embodiment, the method comprises administering a miR-451 mimetic to the subject. The miR-451 mimetic can be a polynucleotide comprising a mature miR-451 sequence, a precursor miR-451 sequence, or a primary miR-451 sequence. In some embodiments, a polynucleotide comprising a miR-451 sequence is expressed from a vector. The subject may be diagnosed with, suffering from, or at risk of developing a red cell aplasia or a type of anemia, such as aplastic anemia.

The present invention also provides a method of modulating the ratio of mature erythrocytes to erythrocyte precursors in a subject. In one embodiment, the method comprises administering a modulator of miR-451 activity or expression to the subject. A decrease in the ratio of mature erythrocytes to erythrocyte precursors can be achieved by administering a miR-451 inhibitor of the invention. An increase in the ratio of mature erythrocytes to erythrocyte precursors can be achieved by administering a miR-451 mimetic of the invention. In some embodiments, the mature erythrocytes are CD71 negative and TER 119 positive.

BRIEF DESCRIPTION OF THE DRAWINGS

FIG. 6. A. Flow cytometry analysis of bone marrow isolated from adult wild-type (miR-451+/+), miR-451 heterozygotes (miR-451+/−), and miR-451 knockout (miR-451−/−) animals. CD71+ cells are shown on the y-axis and TER119+ cells are shown on the x-axis. B. Percentage of CD71−/TER119+ mature erythrocytes (Region IV) in bone marrow tissue from wild-type (miR-451+/+), miR-451 heterozygotes (miR-451+/−), and miR-451 knockout (miR-451−/−) animals.

FIG. 8. A. Schematic showing conserved 3'-UTR binding sites among different species (SEQ ID NOs: 11-14) for miR-451 (SEQ ID NO: 3) in YWHAZ. The miR-451 seed region is highlighted in red. B. Real time RT-PCR analysis shows significant upregulation of the YWHAZ transcript in miR-451 knockout (KO) animals with no significant changes in other transcripts encoding for 14-3-3 proteins as compared to wild-type (WT) animals.

DETAILED DESCRIPTION OF THE INVENTION

Figure 1:
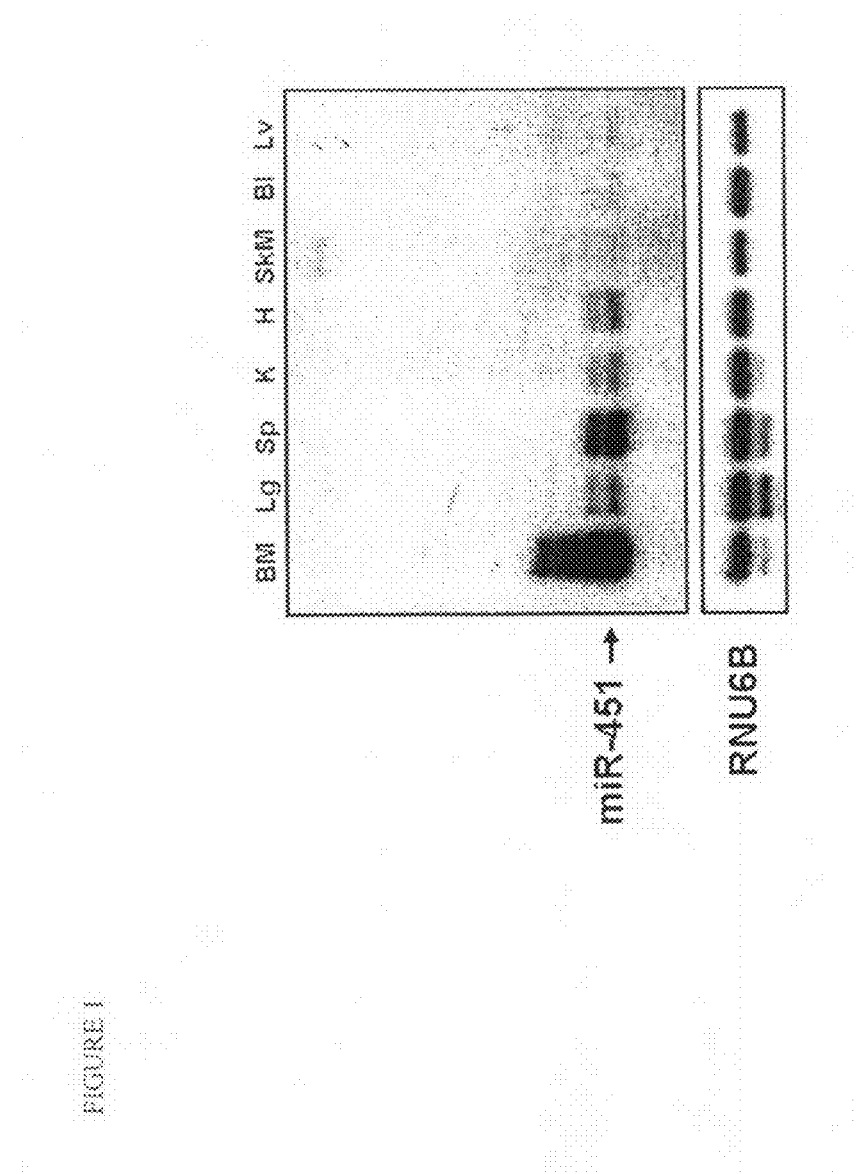
FIG. 1. Northern blot analysis of miR-451 expression in the indicated tissues isolated from wild-type mice. BM, bone marrow; Lg, lung; Sp, spleen; K, kidney; H, heart; SkM, skeletal muscle; Bl, bladder; Lv, liver.

The present invention is based, in part, on the discovery that miR-451 is required for mammalian erythrocyte maturation. Mice lacking both miR-451 alleles exhibit a nearly complete elimination of mature erythrocytes, while heterozygote animals have approximately half the normal level of mature erythrocytes. Therefore, modulation of miR-451 expression can be employed to regulate mature erythrocyte or red blood cell production. Accordingly, the present invention provides methods of treating diseases and disorders associated with aberrant levels of mature red blood cells, such as polycythemia and anemia.

In humans, miR-451 is expressed with miR-144 from an intergenic region of chromosome 17. The pre-miRNA encoding sequences for miR-451 for human and mouse are shown below as SEQ ID NO: 1 and SEQ ID NO: 2, respectively. The mature miR-451 sequence is provided in SEQ ID NO: 3. The mouse pri-miR-144/451 sequence is provided in SEQ ID NO: 15. The predicted pri-miR-144/451 sequence location is on chromosome 17 at genomic coordinates 24212513-24212762 (Saini et al. (2008) BMC Genomics, Vol 9: 564, which is herein incorporated by reference). The invention also includes use of the human pri-miR-144/451 sequence.

```
Human pre-miR-451
                                            (SEQ ID NO: 1)
5'-CUUGGGAAUG GCAAGGAAAC CGUUACCAUU ACUGAGUUUA

GUAAUGGUAA UGGUUCUCUU GCUAUACCCA GA-3'

Mouse pre-miR-451
                                            (SEQ ID NO: 2)
5'-CUUGGGAAUG GCGAGGAAAC CGUUACCAUU ACUGAGUUUA

GUAAUGGUAA CGGUUCUCUU GCUGCUCCCA CA-3'

Mature miR-451
                                            (SEQ ID NO: 3)
5'-AAACCGUUAC CAUUACUGAG UU-3'

Mouse pri-miR-144/451
                                           (SEQ ID NO: 15)
5'-CAGGCTCTCCCTGTGCAGAGGATTCCCTGGACGAGGCTCCAGCTC

CACTCCAGCTCCAGGTAAGCAGTCCTTGGAGTGGCTGTCAGCCTGCTT

ATAGGTCTGCCCAGAGGGAAGCTCCTGCCTCACAACTTCGTTTCTGCC

TGTAACTCTGGATCCCTAAGAGACCCGAGTAGACCTTAGCTTCCTTCT

CTAAGCCACCTGGGGTTATCCTGGACCACAGGATCAGGGAGATGCTGC

TCTGGGAGGGAAGTGGAGGAGCAGAGGTAGGGACTTAGGTGTCCCTGA

CTGACCCTGAGCCAATCCCCTGGCTCACTCCAGGCCTGCTGCTCACCT

CCTCCTCCAGGACCTTGGCTGGGATATCATCATATACTGTAAGTTTGT

GATGAGACACTACAGTATAGATGATGTACTAGTCTGGGTACCCCACCT

CCAGAGCCTGCCTGGTTTGCAGCAGAGATGCAGAAGTACACGGGCTCA

CTGCTCGGCCTAATCAAGCCTGCTGACAGCTGTGGCACTTGGGAATGG

CGAGGAAACCGTTACCATTACTGAGTTTAGTAATGGTAACGGTTCTCT

TGCTGCTCCCACAAACTGTGCCAAGAAGAGCTCATGACCCTGGAGCAG

ACTGCTGGAAGAAAAGGACACCCAGGCTGACAAGAGAATGGGGTTGGG

GGAAAGGGTACATTTTCCTCTTCACTGTGCCAAAGAAATAAAAGATAA

GAATAAGAGCACTTGTCATTTAACTTTATTAGCATCCGAGGCTGGGTG

GTTGGATG-3'
```

It is understood that when the RNA sequences disclosed herein are used in embodiments that require deoxyribonucleotides, a thymidine residue is substituted for a uridine residue. Similarly, when the DNA sequences disclosed herein are used in embodiments that require ribonucleotides, a uridine residue is substituted for a thymidine residue.

In one embodiment, the present invention provides a method of treating polycythemia in a subject in need thereof by administering an inhibitor of miR-451 activity or expression. As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

Polycythemia is a myeloproliferative disorder characterized by an increase in red blood cell mass. Primary polycythemia or polycythemia vera is thought to be caused by an abnormality in the bone marrow which results in the excess production of red blood cells. The methods of the present invention provide a treatment for polycythemia by administering to a subject in need thereof a miR-451 inhibitor, thereby resulting in a decrease in the number of mature erythrocytes or red blood cells. In one embodiment, the subject's red blood cell count is reduced following administration of the inhibitor of miR-451 as compared to a subject not receiving the miR-451 inhibitor. For instance, the subject's red blood cell count may be reduced by about 10%, 20%, 30%, or about 40% following administration of the miR-451 inhibitor as compared to a subject not receiving the miR-451 inhibitor. In another embodiment, the subject's red blood cell count is reduced to within a normal red count level. A normal red blood cell count is about 4.2 to about 5.4 million cells/µL for women, about 4.7 to about 6.1 million cells/µL for men, and about 4.6 to about 4.8 million cells/µL for children. In certain embodiments, the subject is diagnosed with, suffering from, or at risk of developing polycythemia vera, primary familial and congenital polycythemia, or a disease associated with polycythemia. Diseases associated with polycythemia include, but are not limited to, emphysema, chronic obstructive pulmonary disease (COPD), congestive heart failure, sleep apnea, multiple myeloma, or pulmonary hypertension. Thus, the present invention also encompasses methods of treating diseases associated with polycythemia by administering a miR-451 inhibitor.

In another embodiment, the present invention includes a method of treating or preventing other myeloproliferative disorders in a subject by administering a miR-451 inhibitor. For instance, in one embodiment, the present invention provides a method of treating essential thrombocythemia (also referred to as essential thromobocytosis) in a subject in need thereof comprising administering to the subject a miR-451 inhibitor. Essential thrombocythemia is a disease characterized by the overproduction of platelets. In some embodiments, the subject's platelet count is reduced following administration of the miR-451 inhibitor as compared to the platelet count in a subject not receiving the miR-451 inhibitor. In other embodiments, a reduction in splenic enlargement occurs in the subject following administration of the miR-451 inhibitor as compared to a subject not receiving the miR-451 inhibitor.

In another embodiment, the present invention provides a method of treating or preventing myelofibrosis in a subject in need thereof comprising administering to the subject a miR-451 inhibitor. The bone marrow of patients suffering from primary or idiopathic myelofibrosis is replaced with collagenous connective tissue fibers causing a progressive pancytopenia. In certain embodiments, the fibrous content of the subject's bone marrow is reduced following administration of the miR-451 inhibitor as compared to a subject not receiving the miR-451 inhibitor. In other embodiments, the subject's red blood cell, white blood cell, and/or platelet count is increased following administration of the miR-451 inhibitor as compared to a subject not receiving the miR-451 inhibitor.

In yet another embodiment, the present invention provides a method of preventing or treating leukemia in a subject by administering a miR-451 inhibitor. In some embodiments, the subject is diagnosed with, suffering from, or at risk of developing polycythemia vera and is at risk for developing leukemia. In certain embodiments, the leukemia is acute lymphocytic leukemia (ALL). In other embodiments, the leukemia is chronic myelogenous leukemia (CML). In still other embodiments, the leukemia is chronic lymphocytic leukemia (CLL) or acute myelogenous leukemia (AML).

The inhibitor of miR-451 activity or expression can be an antisense oligonucleotide targeting all or part of the mature miR-451 sequence. The antisense oligonucleotide can comprise ribonucleotides, deoxyribonucleotides, or a combination thereof. Preferably, the antisense oligonucleotide has at least one chemical modification (e.g., sugar or backbone modification). For instance, suitable antisense oligonucleotides may be comprised of one or more "conformationally constrained" or bicyclic sugar nucleoside modifications (BSN) that confer enhanced thermal stability to complexes formed between the oligonucleotide containing BSN and their complementary microRNA target strand. For example, in one embodiment, the antisense oligonucleotides contain at least one "locked nucleic acid." Locked nucleic acids (LNAs) contain the 2'-O, 4'-C-methylene ribonucleoside (structure A) wherein the ribose sugar moiety is in a "locked" conformation. In another embodiment, the antisense oligonucleotides contain at least one 2',4'-C-bridged 2' deoxyribonucleoside (cDNA, structure B). See, e.g., U.S. Pat. No. 6,403,566 and Wang et al. (1999) Bioorganic and Medicinal Chemistry Letters, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting miR-451 can contain combinations of BSN (LNA, cDNA and the like) or other modified nucleotides, and ribonucleotides or deoxyribonucleotides.

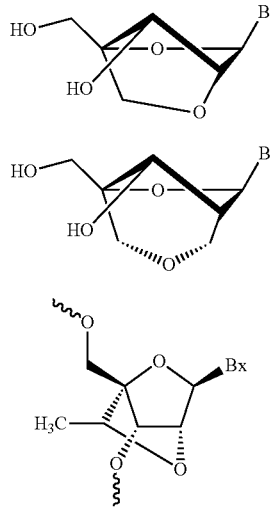

A

B

C

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. For instance, other chemical modifications that the antisense oligonucleotides may contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In one embodiment, antisense oligonucleotides targeting miR-451 contain 2'O-methyl sugar modifications on each base and are linked by phosphorothioate linkages. Antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O-alkyl modifications and the like. In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, to facilitate in vivo delivery and stability, the antisense oligonucleotide may be linked to a steroid, such as cholesterol moiety, a vitamin, a fatty acid, a carbohydrate or glycoside, a peptide, or other small molecule ligand at its 3' end.

Preferable antisense oligonucleotides useful for inhibiting the activity of miRNAs are about 5 to about 25 nucleotides in length, about 10 to about 30 nucleotides in length, or about 20 to about 25 nucleotides in length. In certain embodiments, antisense oligonucleotides targeting miR-451 are about 8 to about 18 nucleotides in length, and in other embodiments about 12 to about 16 nucleotides in length. Any 8-mer or longer complementary to miR-451 may be used, i.e., any antimiR complementary to the 5' end of the miRNA and progressing across the full complementary sequence of the miRNA. For instance, in one embodiment, the antisense oligonucleotide has a sequence of 5'-AACUCAGUAAUG-GUAACGGUUU-3' (SEQ ID NO: 4). In another embodiment, the antisense oligonucleotide has a sequence of 5'-AACGGUUU-3' (SEQ ID NO: 6). In another embodiment, the antisense oligonucleotide has a sequence of 5'-GUAACG-GUUU-3' (SEQ ID NO: 7). In another embodiment, the antisense oligonucleotide has a sequence of 5'-UGGUAACG-GUUU-3' (SEQ ID NO: 8). In yet another embodiment, the antisense oligonucleotide has a sequence of 5'-AAUG-GUAACGGUUU-3' (SEQ ID NO: 9). In still another embodiment, the antisense oligonucleotide has a sequence of 5'-GUAAUGGUAACGGUUU-3' (SEQ ID NO: 10). Other suitable inhibitors of miR-451 are antisense oligonucleotides comprising a sequence selected from the group consisting of 5'-AGUAAUGGUAACGGUU-3' (SEQ ID NO: 16), 5'-GUAAUGGUAACGGUU-3' (SEQ ID NO: 17), 5'-UAAUGGUAACGGUUU-3' (SEQ ID NO: 18), 5'-UAAUGGUAACGGUU-3' (SEQ ID NO: 19), and 5'-UAACGGUU-3' (SEQ ID NO: 20). Antisense oligonucleotides may comprise a sequence that is at least partially complementary to all or a part of a mature miR-451 sequence, e.g. at least about 75%, 80%, 85%, 90%, 95%, 96%, 97%, 98%, or 99% complementary to all or a part of a mature miR-451 sequence. In some embodiments, the antisense oligonucleotide may be substantially complementary to all or part of a mature miR-451 sequence, that is at least about 90%, 95%, 96%, 97%, 98%, or 99% complementary to a target polynucleotide sequence. In one embodiment, the antisense oligonucleotide comprises a sequence that is 100% complementary to all or part of a mature miR-451 sequence. In certain embodiments, the antisense oligonucleotide is at least partially complementary to SEQ ID NO: 3.

Antisense oligonucleotides may comprise a sequence that is at least partially complementary to all or part of a precursor miRNA sequence (pre-miRNA) for miR-451, e.g. at least about 75%, 80%, 85%, 90%, 95%, 96%, 97%, 98%, or 99% complementary to all or a part of a pre-miR-451 sequence. In some embodiments, the antisense oligonucleotide comprises a sequence that is at least partially complementary to a sequence located outside of the stem-loop region of the pre-miR-451. In one embodiment, an inhibitor of miR-451 is an antisense oligonucleotide having a sequence that is at least partially complementary to all or a part of a pre-miR-451 sequence of SEQ ID NO: 1 or SEQ ID NO: 2. In certain embodiments, antisense oligonucleotides may comprise a sequence that is at least partially complementary to all or part of a primary miRNA sequence (pri-miRNA) for miR-451. For instance, in one particular embodiment, an inhibitor of miR-451 is an antisense oligonucleotide having a sequence that is at least partially complementary to all or part of pri-miR-451 sequence of SEQ ID NO: 15 or the corresponding human pri-miR-451 sequence.

The miR-451 inhibitors described herein may be administered with other therapeutic agents used to treat polycythemia (e.g., polycythemia vera) and other myeloproliferative disorders, such as essential thrombocythemia, myelofibrosis, and myeloid leukemias. For instance, the miR-451 may be co-administered with therapeutic agents including, but not limited to, blood thinners (e.g., aspirin), interferon-alpha, anagrelide, hydroxyurea, chemotherapeutic agents, dasatinib (Sprycel), INCB-18424, lestaurtinib (CEP-701), givinostat (ITF-2357), XL-019, MK-0683, pegylated interferon-alpha 2a (Pegasys), TAK-901, and erlotinib. The miR-451 inhibitors may be administered prior to or after administration of the other therapeutic agent. In some embodiments, the miR-451 inhibitor is administered simultaneously with the other therapeutic agent. In certain embodiments, the miR-451 inhibitor is administered prior to or following procedures used to ameliorate myeloproliferative disorders, such as phlebotomy, platelet apheresis, and bone marrow transplants.

The present invention also includes a method of increasing red blood cell count in a subject in need thereof. In one embodiment, the method comprises administering a miR-451 mimetic to the subject. As used herein, a "miR-451 mimetic" is an agent that produces a biological effect conferred by miR-451. A miR-451 mimetic can include agents that are agonists of miR-451 expression or activity or otherwise increase miR-451 function. In certain embodiments, the subject is diagnosed with, suffering from, or at risk of developing anemia, such as a type of microcytic, macrocytic or normocytic anemia. In one embodiment, the subject is diagnosed with, suffering from, or at risk of developing aplastic anemia or red cell aplasia. In another embodiment, the subject is diagnosed with, suffering from, or at risk of developing a nutrient deficiency, such as an iron deficiency, Vitamin B12 deficiency, or a folate deficiency. In yet another embodiment, the subject is diagnosed with, suffering from, or at risk of developing hemolytic anemia.

The miR-451 mimetic may be administered with other known therapeutic agents for increasing red blood cell count or treating various types of anemia. For example, the miR-451 mimetic may be administered with erythropoietin, oral iron supplementation (e.g., with ferrous sulfate, ferrous fumarate, or ferrous gluconate), folic acid, Vitamin B12, or epoetin alfa. The miR-451 mimetic treatment may also occur with other procedures for treating anemia, such as blood transfusion or bone marrow transplant. For instance, in one embodiment, a miR-451 mimetic of the invention may be delivered to hematopoietic progenitor cells obtained from a blood marrow donor or the blood marrow recipient himself prior to implantation into the marrow recipient.

In some embodiments, the miR-451 mimetic or agonist is a polynucleotide encoding a mature miR-451 sequence (SEQ ID NO: 3). In another embodiment, the miR-451 mimetic or agonist may be a polynucleotide comprising the pri-miRNA sequence for miR-451 (e.g., SEQ ID NO: 15). In still another embodiment, the miR-451 mimetic or agonist may be a polynucleotide comprising the pre-miRNA sequence for miR-451. For instance, the polynucleotide may comprise a sequence of SEQ ID NO: 1 or SEQ ID NO: 2. Such polynucleotides may be from about 18 to about 2000 nucleotides in length, about 70 to about 200 nucleotides in length, about 20 to about 50 nucleotides in length, or about 18 to about 25 nucleotides in length. The polynucleotide comprising the mature miR-451, pre-miR-451, or pri-miR-451 sequence may be single stranded or double-stranded. The polynucleotides may contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-451 sequence is conjugated to a steroid, such as cholesterol, a vitamin, a fatty acid, a carbohydrate or glycoside, a peptide, or another small molecule ligand.

In certain embodiments, the polynucleotide comprising a mature miR-451, pre-miR-451, or pri-miR-451 sequence can be expressed from an expression vector. Additionally, any of the inhibitors of miR-451 described herein can be delivered to the subject by administering an expression vector encoding the miR-451 inhibitor. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. In one embodiment, the vector is a viral vector. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing a polynucleotide comprising a miR-451 sequence comprises a promoter operably linked to a polynucleotide comprising a mature miR-451 sequence (e.g., SEQ ID NO: 3), a pre-miR-451 sequence (e.g., SEQ ID NO: 1 or SEQ ID NO: 2), or a pri-miR-451 sequence (e.g., SEQ ID NO: 15). In another embodiment, an expression vector for expressing a miR-451 inhibitor of the invention comprises a promoter operably linked to a polynucleotide encoding an antisense oligonucleotide, wherein the sequence of the expressed antisense oligonucleotide is partially or perfectly complementary to a mature sequence of miR-451 (e.g., SEQ ID NO: 3). The phrase "operably linked" or "under transcriptional control" as used herein means that the promoter is in the correct location and orientation in relation to a polynucleotide to control the initiation of transcription by RNA polymerase and expression of the polynucleotide. As used herein, a "promoter" refers to a DNA sequence recognized by the synthetic machinery of the cell, or introduced synthetic machinery, required to initiate the specific transcription of a gene. Suitable promoters include, but are not limited to RNA pol I, pol II, pol III, and viral promoters (e.g. human cytomegalovirus (CMV) immediate early gene promoter, the SV40 early promoter, and the Rous sarcoma virus long terminal repeat). In one embodiment, the promoter is a tissue specific promoter. Of particular interest are erythrocyte progenitor cell promoters, and more particularly, erythrocyte-specific promoters, such as the HK1 (de Vooght et al. (2009) Haematologica, Vol. 94: 1203-1210), GATA1, GATA2, CEBP/alpha, PU.1, and STAT5 promoters. In certain embodiments, the promoter operably linked to a polynucleotide encoding miR-451 or a miR-451 inhibitor may be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR.

The present invention also provides a method of modulating the ratio of mature erythrocytes to erythrocyte precursors in a subject. In one embodiment, the method comprises administering a modulator of miR-451 activity or expression to the subject. A "modulator of miR-451 activity or expression" includes agents that inhibit or decrease miR-451 activity or expression, such as the miR-451 inhibitors as described herein. Modulators of miR-451 activity or expression also include miR-451 agonists or mimetics, such as polynucleotides comprising miR-451 sequences (e.g., mature miR-451, pre-miR-451, or pri-miR-451) or agents that increase miR-451 expression, such as transcription factors or growth factors.

As used herein, "mature erythrocytes" refers to terminally differentiated red blood cells. In some embodiments, the mature erythrocytes are CD71 negative and TER 119 positive. "Erythrocyte precursors" refers to progenitor cells, including BFU-E and CFU-E, that generate reticulocytes and mature red blood cells. Erythrocyte precursors are typically positive for CD71, the erythropoietin receptor, and c-kit. In one embodiment, the modulator is a miR-451 inhibitor and the ratio of mature erythrocytes to erythrocyte precursors is decreased in the subject following administration of the miR-451 inhibitor. Any of the miR-451 inhibitors described herein, such as modified or unmodified antisense oligonucleotides comprising a sequence that is at least partially complementary to all or a portion of a miR-451 sequence, are suitable for use in the method.

In another embodiment, the modulator is a miR-451 mimetic and the ratio of mature erythrocytes to erythrocyte precursors is increased in the subject following administration of the miR-451 mimetic. In one embodiment, the miR-451 mimetic is a polynucleotide comprising a mature miR-451 sequence. Other suitable miR-451 mimetics are described herein and include expression vectors comprising polynucleotides encoding miR-451 sequences.

The present invention also encompasses methods for scavenging or clearing miR-451 inhibitors following treatment. The method may comprise administering a miR-451 mimetic or a polynucleotide comprising binding sites for the miR-451 inhibitors. In another embodiment, the present invention provides a method for scavenging or clearing miR-451 mimetics following treatment. For instance, a miR-451 inhibitor or a polynucleotide comprising a binding region from a miR-451 target may be administered to scavenge miR-451 mimetics. The binding site regions preferably contains a sequence complementary to the seed region for miR-451. The seed region is the 5' portion of a miRNA spanning bases 2-8 of a mature miRNA, which is important for target recognition. In some embodiments, the binding site region may contain a sequence from the 3'UTR of one or more targets of miR-451, such as YWHAZ (14-3-3 zeta), CAB39, VAPA, or CUGBP2.

The present invention also includes a method of regulating expression of YWHAZ (14-3-3 zeta), CAB39, VAPA, or CUGBP2 in a cell comprising contacting the cell with a modulator of miR-451. In one embodiment, the expression of YWHAZ (14-3-3 zeta), CAB39, VAPA, or CUGBP2 is decreased in the cell following administration of a miR-451 mimetic. In another embodiment, the expression of YWHAZ (14-3-3 zeta), CAB39, VAPA, or CUGBP2 is increased in the cell following administration of a miR-451 inhibitor. The cell can be in vitro or in vivo. In one embodiment, the cell is an erythrocyte precursor, a reticulocyte, or an erythrocyte.

The present invention also encompasses pharmaceutical compositions comprising an inhibitor or mimetic of miR-451 and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

In one embodiment, the pharmaceutical composition comprises an effective dose of a miR-451 inhibitor. For instance, the pharmaceutical composition comprises and effective dose of a modified or unmodified antisense oligonucleotide targeting miR-451 as described herein. In some embodiments, the pharmaceutical composition comprises a modified or unmodified antisense oligonucleotide having a sequence selected from the group consisting of SEQ ID NO: 4, SEQ ID NO: 6, SEQ ID NO: 7, SEQ ID NO: 8, SEQ ID NO: 9, SEQ ID NO: 10, SEQ ID NO: 16, SEQ ID NO: 17, SEQ ID NO: 18, SEQ ID NO: 19, and SEQ ID NO: 20. In another embodiment, the pharmaceutical composition comprises an effective dose of a miR-451 mimetic or miR-451 agonist. An "effective dose" is an amount sufficient to effect a beneficial or desired clinical result. An effective dose of an miRNA inhibitor or miRNA agonist/mimetic of the invention may be about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of disorder to be treated (e.g. polycythemia or particular type of anemia), and nature of inhibitor or agonist (e.g. expression construct, antisense oligonucleotide, polynucleotide duplex, etc). Therefore, dosages can be readily ascertained by those of ordinary skill in the art from this disclosure and the knowledge in the art. In some embodiments, multiple doses are administered to the subject over a particular treatment period. For instance, a dose of a miR-451 inhibitor or miR-451 mimetic/agonist can be administered to a subject daily, weekly, monthly, every two months, every three months, or every six months. In certain embodiments, the subject receives an initial dose at a first time point that is higher than one or more subsequent or maintenance doses.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of miRNA function, polynucleotides encoding miRNA agonists, or constructs expressing particular miRNA inhibitors or agonists. Commercially available fat emulsions that are suitable for delivering the nucleic acids of the invention to a subject include Intralipid®, Liposyn®, Liposyn® II, Liposyn® III, Nutrilipid, and other similar lipid emulsions. A preferred colloidal system for use as a delivery vehicle in viva is a liposome (i.e., an artificial membrane vesicle). The preparation and use of such systems is well known in the art. Exemplary formulations are also disclosed in U.S. Pat. No. 5,981, 505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides or miRNA polynucleotide sequences (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection. In certain embodiments, the pharmaceutical compositions of the invention are formulated for intravenous or subcutaneous administration. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids), or from organic acids (e.g., acetic, oxalic, tartaric, mandelic), and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine) and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1

MiR-451 Knockout Mice Exhibit a Deficit in Erythrocyte Maturation

MiR-451 expression was assessed by Northern blot analysis in various tissues of wild-type mice, and was found to be highly expressed in hematopoietic tissues including the spleen and bone marrow (FIG. 1). To further examine the function of miR-451 in such tissues, miR-451 knockout mice were created. To generate the miR-451 targeting vector, a 4.3 kb fragment (5' arm) extending upstream of a poorly conserved DNA element located between the miR-144 and miR-451 pre-miR sequences was digested with SacII and NotI and ligated into the pGKneoF2L2dta targeting plasmid upstream of the loxP sites and the Frt-flanked neomycin cassette. A 3.2 kb fragment (3' arm) extending downstream from a poorly conserved region outside of the miR-451 pre-miR was digested with SalI and HindIII and ligated into the vector between the neomycin resistance and Dta negative selection cassettes. Targeted ES-cells carrying the disrupted allele were identified by Southern blot analysis with 5' and 3' probes. Three miR-451 targeted ES clones were identified and used for blastocyst injection. The resulting chimeric mice were bred to C57BL/6 to obtain germline transmission of the mutant allele. miR-451 global mutant mice were generated by breeding miR-451$^{neo/neo}$ mice to C57BL/6 mice harboring the ubiquitously expressed CAG-cre transgene.

Figure 2:
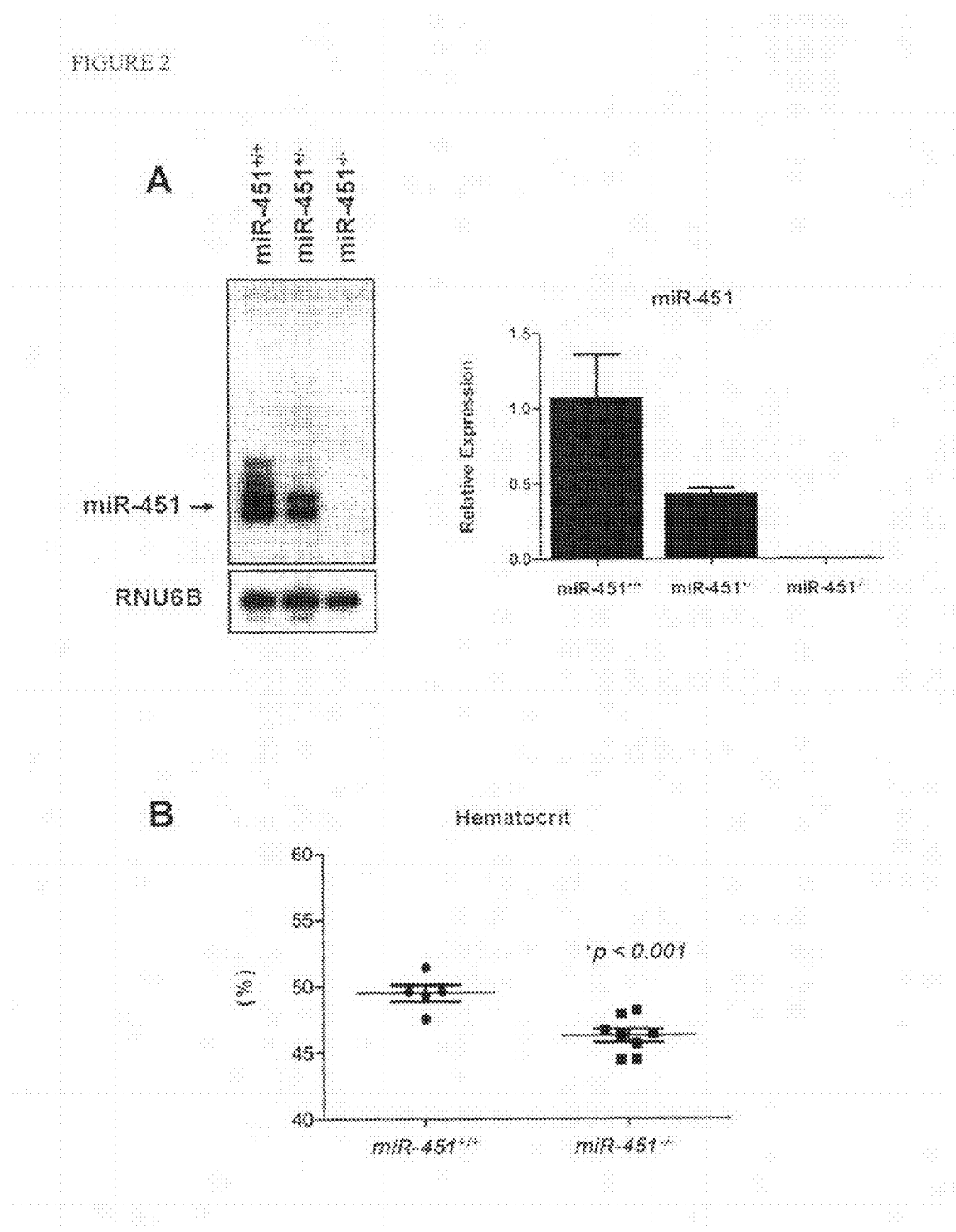
FIG. 2. A. Northern blot (left panel) and quantitative real-time RT-PCR analysis (right panel) of miR-451 expression in bone marrow tissue isolated from wild-type (WT; miR-451+/+), heterozygote (Het; miR-451+/−), and miR-451 knockout (KO; miR-451−/−) animals. RNU6B expression was used as a loading control. B. Hematocrit levels in 8-week old wild-type (WT; miR-451+/+) mice and mice lacking both miR-451 alleles (KO; miR-451−/−).
Figure 3:
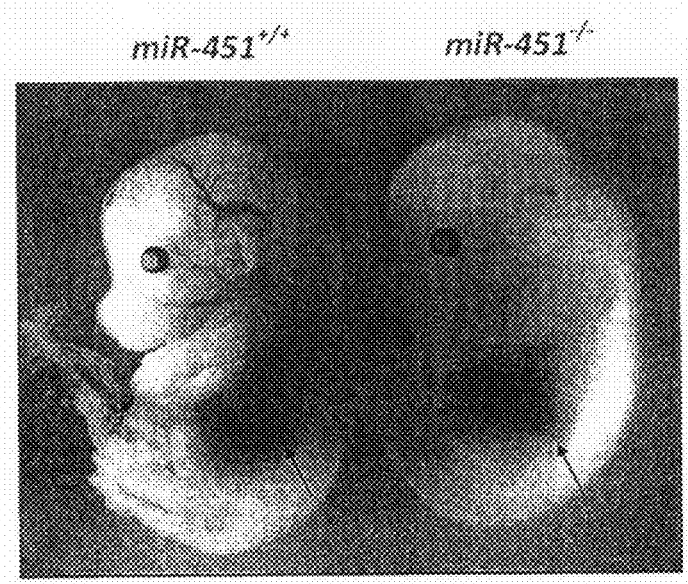
FIG. 3. Whole mount wild-type (miR-451+/+) or miR-451 knockout (miR-451−/−) embryos at E14.5. Arrows indicate fetal liver. miR-451 knockout embryos display pallor and a reduction in the size of the fetal liver.

Targeted deletion of miR-451 revealed haploinsufficient levels of miR-451 in bone marrow in miR-451 heterozygous animals, and complete loss of mature miR-451 in miR-451 knockout (KO) animals (FIG. 2A). MiR-451 KO animals were born at Mendelian ratios (Table 1). However, hematocrit in adult knockout animals (8 weeks old) was significantly reduced compared to wild-type littermates (FIG. 2B). In addition, miR-451 KO animals displayed fetal anemia at embryonic day E14.5 as evidenced by whole mount analysis (FIG. 3).

TABLE 1

Offspring distribution resulting from a miR-451 heterozygote cross

| miR-451 Genotype (14 animals) | Wild-Type | Heterozygote | Knockout |
|---|---|---|---|
| Expected | 3.5 (25%) | 7 (50%) | 3.5 (25%) |
| Observed | 2 (14%) | 9 (64%) | 3 (22%) |

Figure 4:
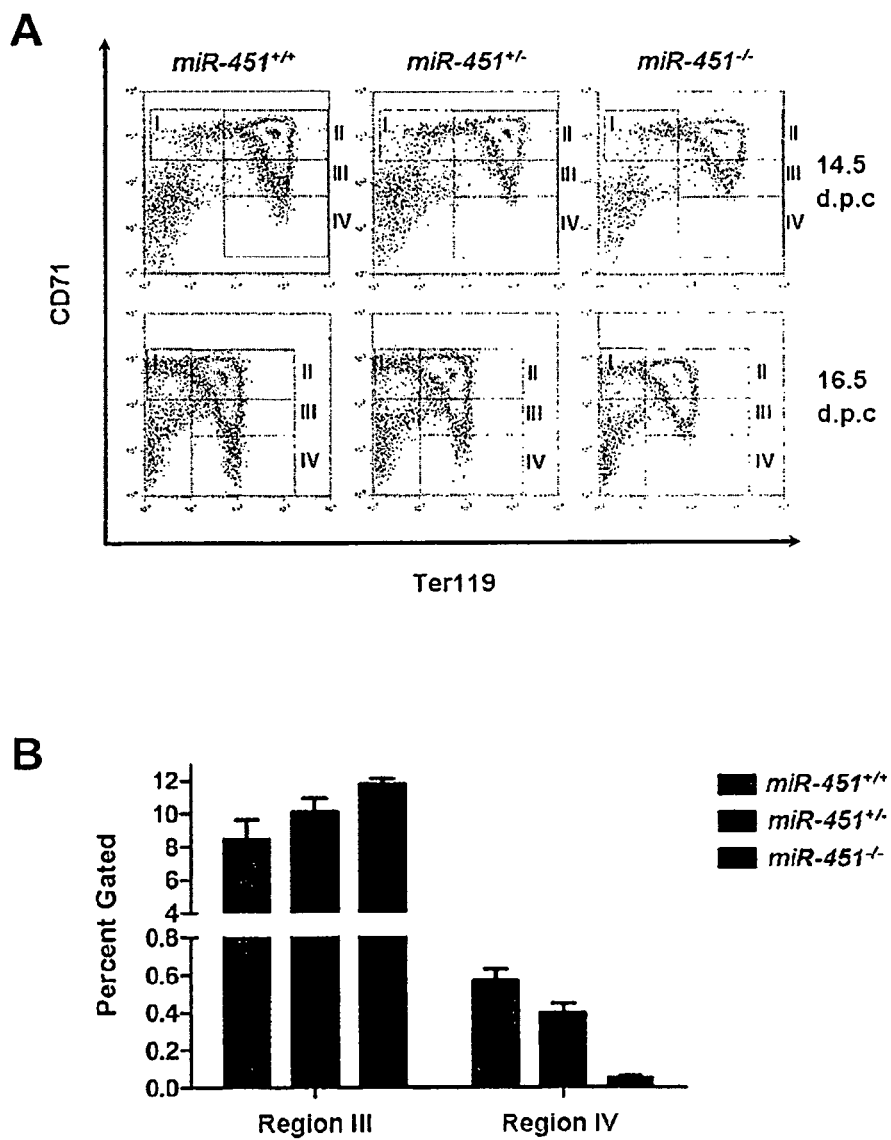
FIG. 4. A: Flow cytometry analysis of erythrocytes isolated from wild-type (miR-451+/+), miR-451 heterozygotes (miR-451+/−), and miR-451 knockout (miR-451−/−) animals on days 14.5 and 16.5 post coitus. CD71+ cells are shown on the y-axis and TER119+ cells are shown on the x-axis. B. Percentage of erythrocytes in regions III and IV representing immature and mature erythrocytes respectively from WT (miR-451+/+), miR-451 Het (miR-451+/−), and miR-451 KO (miR-451−/−) animals at 16.5 d.p.c.
Figure 5:
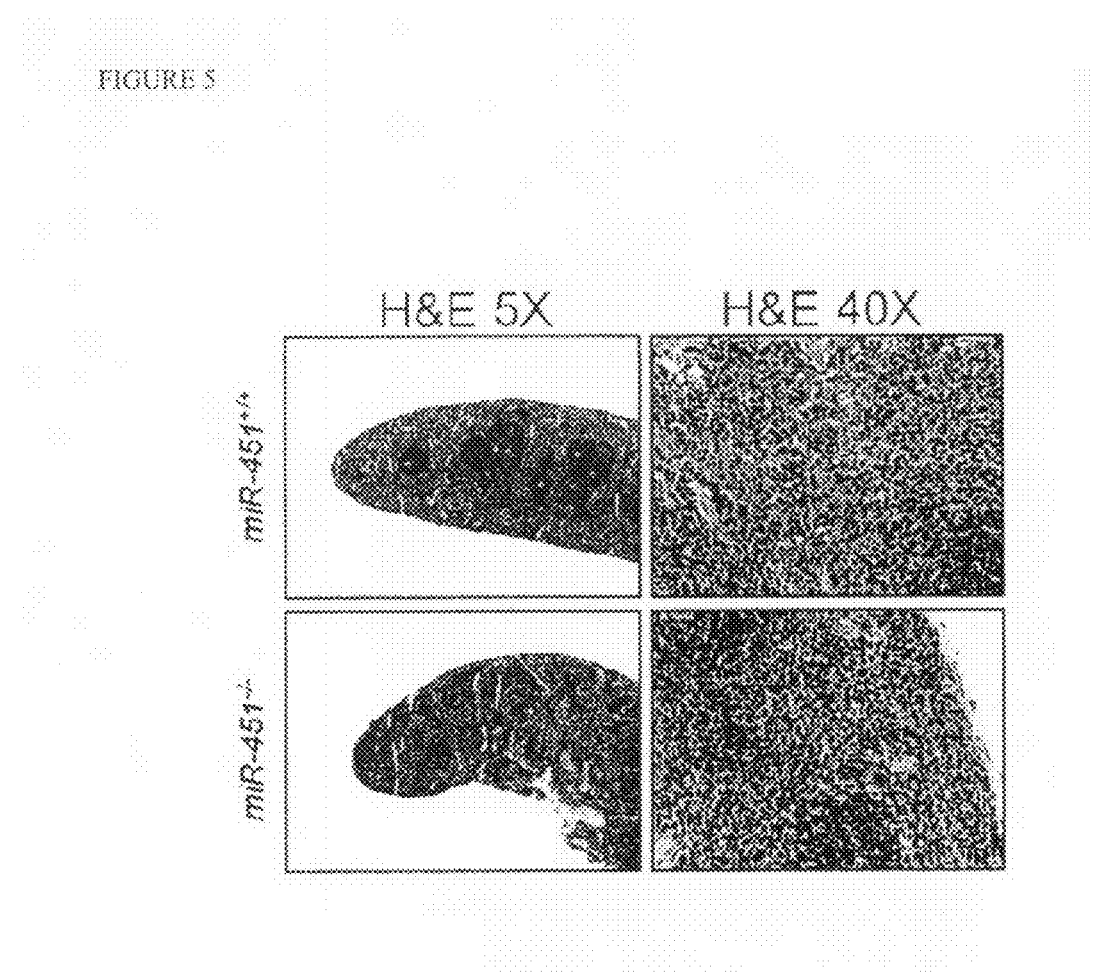
FIG. 5. Histological sections of spleen isolated from adult wild-type (miR-451+/+) or miR-451 knockout (miR-451−/−) mice magnified at 5× (left panel) or 40× (right panel). Sections were stained with hematoxylin and eosin. miR-451 knockout spleen displays significant expansion of erythrocyte precursors.

Animals lacking one or both miR-451 alleles exhibited a defect in erythrocyte maturation. Bone marrow and fetal liver cells isolated from miR-451 wild-type, heterozygote, and knockout mice were resuspended in DMEM/10% FBS. Freshly isolated bone marrow and fetal liver cells were immunostained at 4° C. in PBS/2% FBS in the presence of mouse IgG (200 μg/mL, BD Pharmingen, San Diego, Calif.) to block Fc receptors. Cells were incubated with PE-conjugated anti-Ter119 (1 μg/mL BD Pharmingen, San Diego, Calif.), FITC-conjugated anti-CD71 (EBiosciences, 1 μg/mL, City) antibodies for 15 minutes, followed by a 15-minute incubation with APC-conjugated annexin V. Flow cytometry was carried out on a Becton Dickinson FACSCalibur (Franklin Lakes, N.J.). At embryonic day E16.5, there was a significant decrease in the mature CD71$^-$/TER119$^+$ erythrocyte population in the heterozygous animals with an exaggerated decrease in the knockout animals as assessed by flow cytometry (FIGS. 4A and B). Histologic analysis of adult spleen revealed increased erythrocyte precursors in the miR-451 knockout mice as compared to wild-type litter mates (FIG. 5). Flow cytometric analysis of adult bone marrow revealed a similar erythrocyte differentiation defect with a decrease in the mature CD71$^-$/TER119$^+$ erythrocyte population in the heterozygous animals, and an exaggerated decrease in the knockouts (FIGS. 6A and B).

Figure 7:
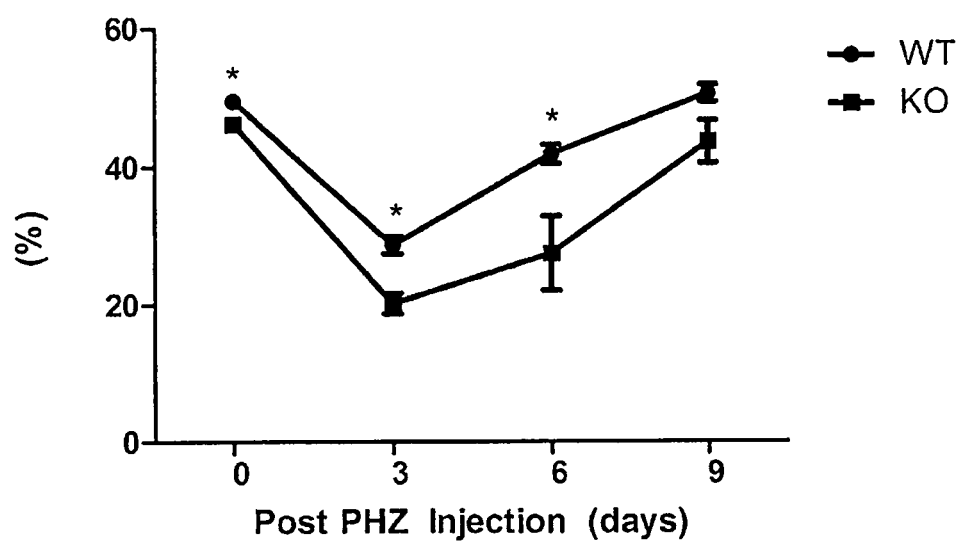
FIG. 7. Hematocrit of miR-451 wild-type (WT) and knockout (KO) animals after phenylhydrazine (PHZ) hemolysis stress study. miR-451 animals display deficiency in generating a high erythropoietic rate.

To assess erythropoiesis in miR-451 knockout animals, both wild-type and miR-451 knockout animals were challenged with the hemolytic agent, phenylhydrazine. Phenylhydrazine was injected subcutaneously at a 40 mg/kg dose as previously described (Socolovsky et al. (2001) Blood, Vol. 98: 3261-3273). Hematocrit was measured in the treated animals at 3, 6, and 9 days following phenylhydrazine injection. As shown in FIG. 7, miR-451 knockout animals exhibited a significant deficit in hematocrit following phenylhydrazine challenge, suggesting that miR-451 knockout animals are unable to achieve a high erythropoietic rate.

Figure 9:
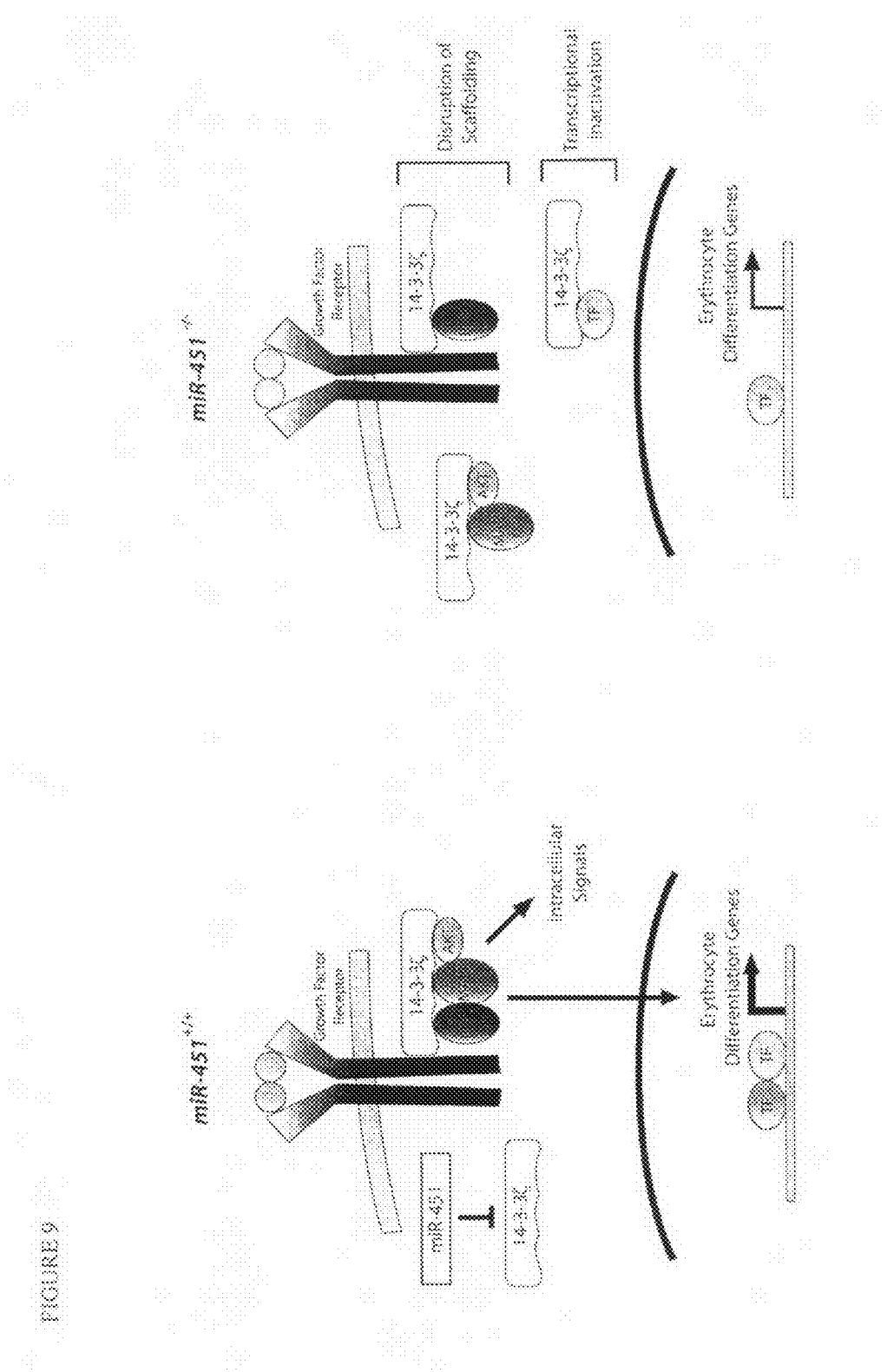
FIG. 9. Schematic of possible regulation pathway of erythrocyte differentiation by miR-451. MiR-451 may inhibit expression of YWHAZ, the gene encoding the chaperone molecule 14-3-3 zeta, thereby disrupting downstream signaling from growth factor receptors.

These data indicate that miR-451 definitively regulates the process of erythrocyte differentiation. To further elucidate the mechanism by which miR-451 regulates erythrocyte differentiation, target prediction software was used to identify potential targets of miR-451. Based on this analysis, miR-451 may regulate erythrocyte differentiation by inhibiting the expression of the chaperone/scaffolding molecule, YWHAZ (14-3-3 zeta). YWHAZ (14-3-3 zeta) contains a conserved miR-451 binding site in its 3' UTR (FIG. 8A) and expression of this protein is significantly upregulated in miR-451 knockout animals (FIG. 8B). YWHAZ (14-3-3 zeta) has been shown to be highly enriched in hematopoietic cells and likely affects the differentiation of RBCs by modulating signals downstream of growth factor receptors (FIG. 9), such as the erythropoietin (EPO) receptor (Barry et al. (2009) J. Biol. Chem., Vol. 284: 12080-12090).

Example 2

Figure 10:
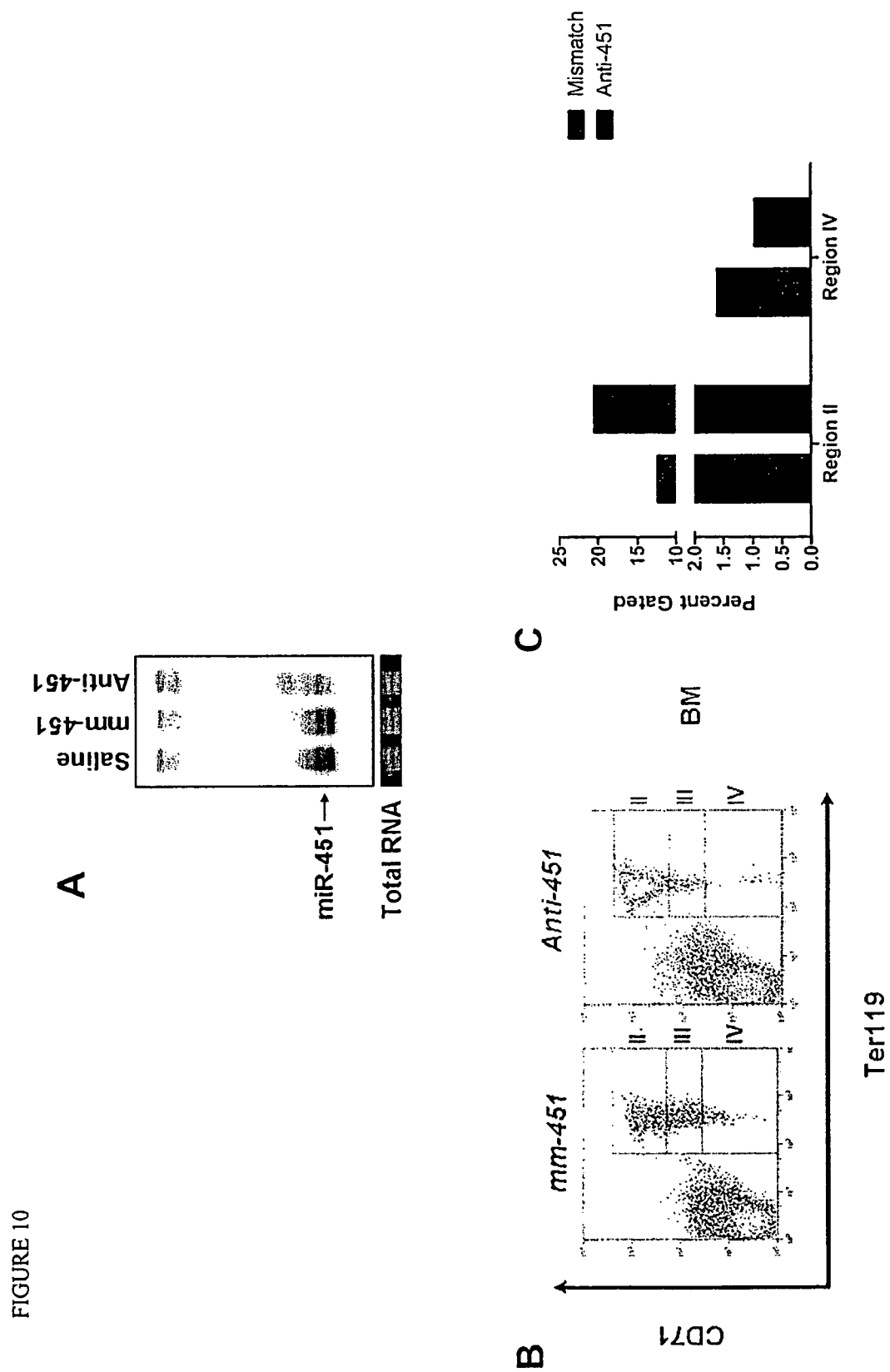
FIG. 10. A. Northern blot analysis from bone marrow isolated from mice injected intravenously with a mismatched control antisense oligonucleotide (mm-451) or an antisense oligonucleotide (anti-451) having a complementary sequence to mature miR-451. B. Flow cytometry analysis of bone marrow isolated animals injected with a mismatched control antisense oligonucleotide (mm-451) or an antisense oligonucleotide targeting miR-451 (anti-451). CD71+ cells are shown on the y-axis and TER119+ cells are shown on the x-axis. C. Percentage of erythrocytes in region II and IV representing immature and terminally differentiated erythrocytes respectively.

An Antisense Oligonucleotide Targeting miR-451 Eliminates miR-451 Expression and Reduces the Number of Mature Erythrocytes In Vivo To examine the therapeutic potential of miR-451 knockdown in disorders associated with aberrant erythropoiesis, we designed an antisense oligonucleotide (anti-451) to specifically induce the degradation of miR-451. The antisense oligonucleotide was complementary to the mature miR-451 sequence and had a sequence of 5'-AACUCAGUAAUG-GUAACGGUUU-3' (SEQ ID NO: 4). A mismatched sequence 5'-AACAGUAAUGGUAACGGUUU-3' (SEQ ID NO: 5) was used as a control. All nucleosides in anti-miR-451 and the mismatched control (mm-451) were 2'-OMe modified, and the 5' terminal two and 3' terminal four bases contained a phosphorothioate internucleoside. Cholesterol was attached to the 3' end of the passenger strand through a hydroxyprolinol or hydrocarbon (C4-C8) linker. Wild-type C57BL/6 mice were injected twice intravenously with saline, 80 mg/kg of anti-451, or 80 mg/kg of the mismatched control. The two injections were separated by 24 hours. Bone marrow was harvested from the animals 48 hours after the second injection for expression and FACs analysis. Northern blot analysis of bone marrow for miR-451 demonstrated that anti-451 effectively reduced miR-451 levels in vivo, while the mismatched control had no effect (FIG. 10A). Flow cytometry analysis of bone marrow isolated from the treated animals revealed a decrease in the number of mature CD71−/TER119+ erythrocytes and a corresponding increase in the number of immature erythrocytes in animals treated with the anti-miR-451 oligonucleotide as compared to animals receiving the mismatched control (FIGS. 10B and C).

These results suggest that miR-451 expression can be efficiently modulated in vivo and that miR-451 inhibitors provide a novel therapeutic tool in the treatment of disorders associated with aberrant erythropoiesis, such as polycythemia.

Example 3

Antisense Oligonucleotide Treatment with Truncated Inhibitors Reduces miR-451 Levels and Alters Red Blood Cell Number In Vivo Another series of synthetic oligonucleotides targeting the mature miR-451 sequence were designed that ranged in length from 8 to 16 nucleotides to target the seed region of the microRNA and extend systematically toward the more 3' end of the microRNA. These oligonucleotides contained one or more bicyclic nucleosides (e.g., LNAs) and their sequences are listed below:

```
8 nt oligo:
                                        (SEQ ID NO: 6)
5'-AACGGUUU-3'

10 nt oligo:
                                        (SEQ ID NO: 7)
5'-GUAACGGUUU-3'

12 nt oligo:
                                        (SEQ ID NO: 8)
5'-UGGUAACGGUUU-3'

14 nt oligo:
                                        (SEQ ID NO: 9)
5'-AAUGGUAACGGUUU-3'

16 nt oligo:
                                        (SEQ ID NO: 10)
5'-GUAAUGGUAACGGUUU-3'
```

In addition to the five oligonucleotides listed above, anti-miR-451 oligonucleotides ranging from 14 to 22 nucleotides in length having a sequence that was complementary to the mature miR-451 sequence were also designed. All nucleosides in these anti-miR-451 oligonucleotides were 2'-OMe modified and contained phosphorothioate internucleosides linking all bases.

Mice are injected intravenously with one of the anti-miR-451 oligonucleotides described above and various tissues are collected after 2 days of treatment. Northern blot analysis for miR-451 is conducted to determine the effectiveness of each of the anti-miR-451 oligonucleotides in suppressing miR-451 expression. In addition, bone marrow and blood samples are obtained from treated mice for FACs analysis and determination of hematocrit. The results are expected to show that anti-miR-451 oligonucleotides can effectively suppress miR-451 expression in vivo and the reduction of miR-451 expression will correlate with reduction in hematocrit and the number of mature CD71−/TER119+ erythrocytes.

Example 4

AntimiR-451 Reduces Hematocrit in a Xenograft Model of Polycythemia Vera

To examine the effects of antimiR-451 and mismatch control antimiR oligonucleotides on the expression of miR-451 in vivo, C57BL/6 mice were treated with either saline, 25 mg/kg of a mismatch oligonucleotide, or 25 mg/kg of anti-miR-451 on two consecutive days. The antimiR-451 oligonucleotide was complementary to 16 nucleotides of mature miR-451 and had a sequence of 5'-AGTAATGGTAACG-GTT-3' (SEQ ID NO: 21). The mismatched control antimiR was directed to a *C. elegans* miRNA, which is not expressed in mammals, and had a sequence of 5'-TCCTAGAAAGAG-TAGA-3' (SEQ ID NO: 22). Both antimiR-451 and the mismatched control antimiR contained a combination of deoxyribonucleotides (DNA) and locked nucleic acid (LNA) nucleosides (9 LNAs and 7 DNAs) and contained a fully phosphorothiolated backbone.

Figure 11:
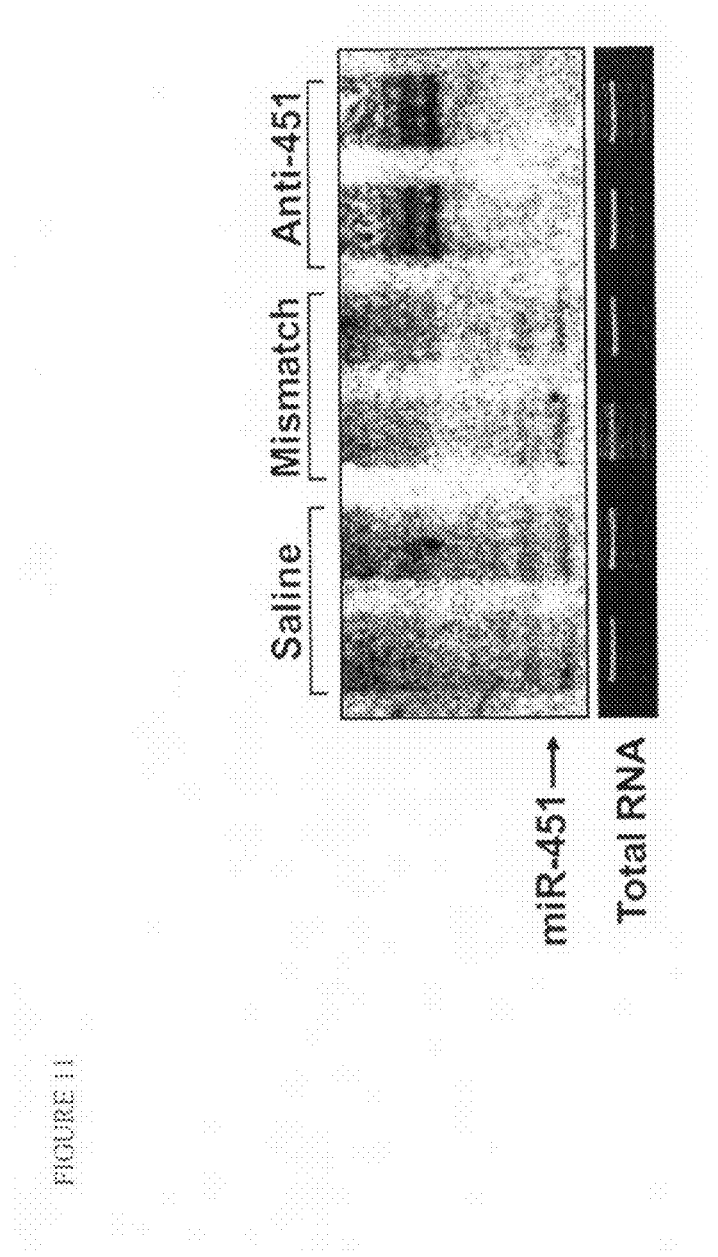
FIG. 11. AntimiR-451 represses miR-451 expression in vivo. Northern blot analysis of RNA harvested from bone marrow of animals treated with either saline, 25 mg/kg mismatch, or mg/kg of antimiR-451 reveals repression of mature miR-451 in only the antimiR-treated group. The ethidium bromide stained acrylamide gel displaying total RNA is shown as a loading control. Each lane represents an individual animal.

Male C57BL/6 mice (8-10 weeks old) were injected twice with saline, 25 mg/kg antimR-451, or 25 mg/kg mismatch control antimiR. Injections were performed 24 hours apart. Mice were sacrificed 48 hours after the second injection and bone marrow was harvested by flushing the femur and tibia with DMEM+10% fetal bovine serum. RNA was harvested from the bone marrow and microRNA northern blots were performed. Northern blot analyses show an absence of the mature miR-451 in the antimiR-451 treated group, however, miR-451 levels were unaffected in either mismatch or saline treated groups (FIG. 11).

To examine the effect of antimiR-451 on polycythemia vera (PV) hematologic parameters, we utilized the murine xenograft model of PV (Wernig et al. (2006) Blood, Vol. 107(11): 4274-4281). This model closely recapitulates many of the parameters of human PV and is a widely accepted mouse model of this disease. Adult congenic BALB/C animals were purchased from Charles River Laboratories. Donor mice were first injected with 5-fluoro uracil to stimulate division of primitive hematopoietic stem cells. Four days later, bone marrow was harvested from these animals, red cells were selectively lysed, and these cells were cultured in a medium containing a cocktail of cytokines designed to support growth and stimulate the expression of viral recognition proteins. The following day, these cells were infected with a retrovirus expressing either JAK2-V617F mutant human kinase or wild-type human JAK2 kinase as a control. Both viral constructs express GFP from an internal ribosomal entry site. These cells were again cultured overnight to allow for viral genome insertion and expression of the respective JAK2 isoform. One day after infection, the infection procedure was repeated and the cells were suspended in a medium suitable for intravenous injection.

Recipient animals were irradiated with 900 cGy and approximately $4-10\times10^5$ resuspended cells were injected intravenously into the recipient animals. These animals were then housed in a sterile environment with administration of antibiotics. Animals were then phlebotomized every 7 days. At these times, the percentage of GFP positive cells was monitored by flow cytometry and hematologic parameters were measured utilizing a Hemavet 850 (Drew Scientific, Dusseldorf Germany). The GFP positivity percentage represents the percentage of transduced engrafted cells. Engraftment and hematologic modifications were noticeable at 2-3 weeks post-transplantation. Engraftment was complete and changes in these parameters were at a steady state at 5 weeks post-transplantation. Expression of wild-type human JAK2 kinase does not have an effect on hematologic parameters and is therefore a suitable control.

Figure 12:
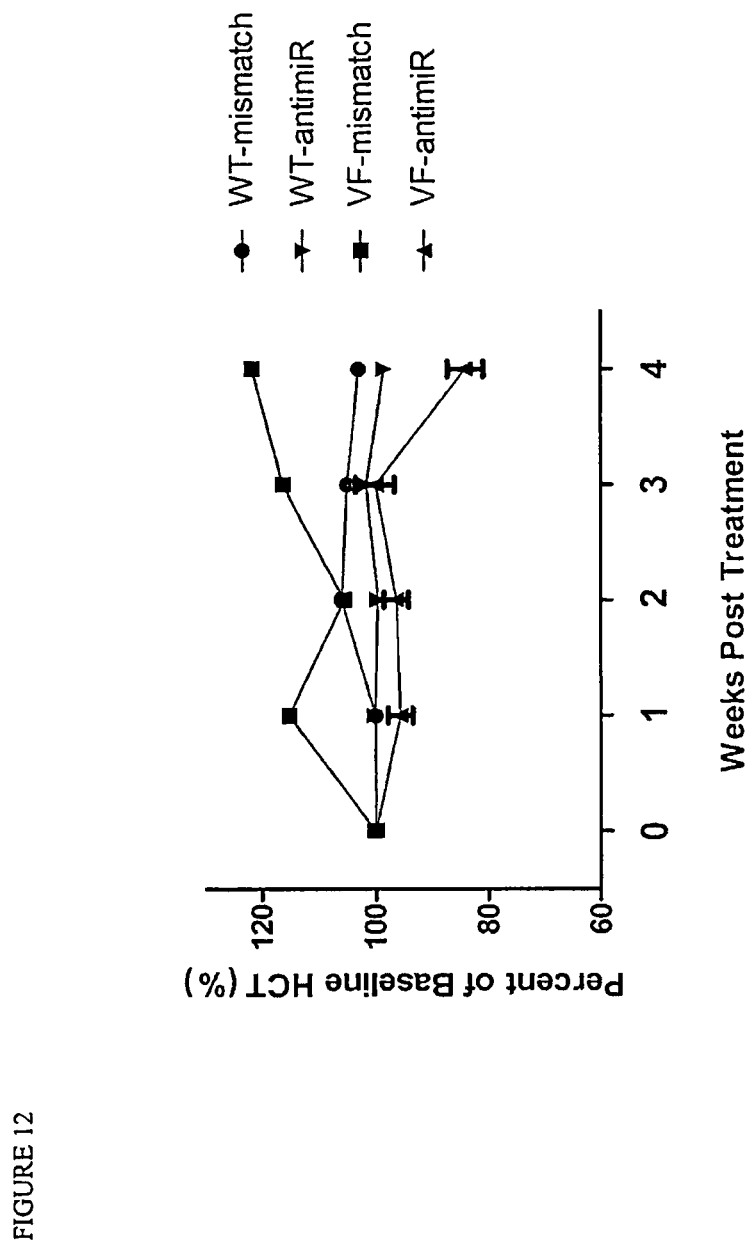
FIG. 12. AntimiR-451 reduces hematocrit in a Xenograft model of PV. Analysis of hematocrit of mice transplanted with stem cells infected with either wild-type human JAK2 kinase (WT) or constitutively active JAK2-V617F (VF) treated with either antimiR-451 (antimiR) or mismatch antimiR (mismatch) reveals a decrease of hematocrit in the VF-antimiR group only. n=1 for WT-mismatch, WT-antimiR, and VF-mismatch. n=4 for VF-antimiR.

At five weeks post-transplantation, both PV and control animals were injected twice on two consecutive days with a loading dose of 25 mg/kg of either antimiR-451 (SEQ ID NO: 21) or mismatch control (SEQ ID NO: 22) oligonucleotide intravenously. These animals were then injected every three days with a lower dose (10 mg/kg) intravenously to maintain sufficient knockdown of miR-451. Hematologic parameters were measured every 7 days using the Hemavet 850 (Drew Scientific, Dusseldorf Germany). Injections and monitoring of hematologic parameters continued for 6-8 weeks after the first injection. Interestingly, we observed a decrease in hematocrit four weeks after the start of antimiR-451 therapy in PV mice (FIG. 12). This decrease was only observed in PV mice treated with antimiR-451 and not PV mice treated with the mismatch control oligonucleotide.

The results of these experiments show that an antisense oligonucleotide targeting the miR-451 mature sequence efficiently suppresses miR-451 expression in vivo and that treatment with an antimiR-451 oligonucleotide reduces hematocrit in a mouse model of PV. Thus, miR-451 represents a novel therapeutic target for the treatment of myeloproliferative disorders, such as polycythemia.

Example 5

AntimiR-451 Attenuates Erythroid Differentiation in Human CD34-Positive Hematopoietic Cells Mice mutant for miR-451 display both an embryonic and adult defect in erythrocyte differentiation (see Example 1). To examine the ability of antimiR-451 to affect the differentiation pattern of human hematopoietic stem cells, we purchased human CD34-positive cells and performed nucleofection of either antimiR-451 (SEQ ID NO: 21) or mismatch control (SEQ ID NO: 22) using the Amaxa Human CD34+ Cell Nucleofector Kit (Lonza, USA). Frozen purified CD34+ human cells were thawed and cultured for 1-2 hours prior to nucleofection. $1 \times 10^6$ cells were plated in single wells of a 12-well plate. Cells were spun at 200×g and resuspended in Nucleofection Solution (Lonza, USA). Next, 100 µL of cell suspension was added to either antimiR-451 or mismatch antimiR (see Example 4 for description of antisense oligonucleotides) resulting in a solution containing a final concentration of 100 nM antimiR-451 or mismatch control. This solution was transferred to a cuvette. Nucleofection was performed with the U-008 program on the Nucleofector device (Lonza, USA). Once the program was finished, cells were combined with 500 µL of culture medium. Medium was then changed every 2-3 days for 10 days.

After nucleofection, cells were incubated for 10 days in culture medium and allowed to differentiate spontaneously. These cells spontaneously differentiate into all hematopoietic cell lineages. On day 10, cells were stained for the erythroid markers CD71 and Ter119 and differentiation was analyzed by flow cytometry. Cells were immunostained at 4° C. in PBS/2% FBS in the presence of mouse IgG (200 µg/mL, BD Pharmingen) to block Fc receptors. Cells were incubated with PE-conjugated anti-Ter119 (1 µg/mL, BD Pharmingen), FITC-conjugated anti-CD71 (EBiosciences, 1 µg/mL) antibodies for 15 minutes. Flow cytometry was carried out on a Becton Dickinson FACSCalibur (Franklin Lakes, N.J.).

Figure 13:
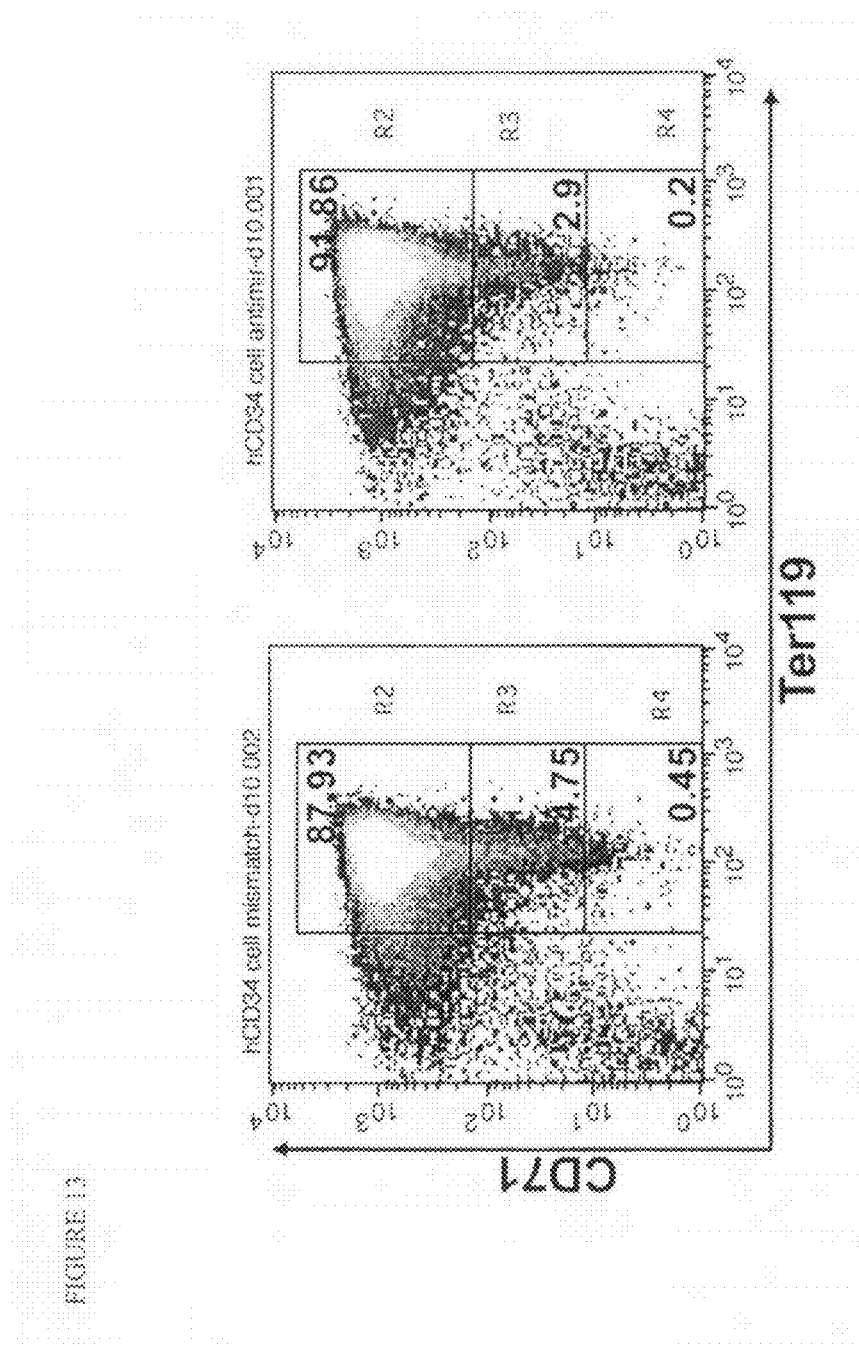
FIG. 13. AntimiR-451 attenuates erythroid differentiation in human CD34-positive hematopoietic cells. Human CD34+ stem cells were nucleofected with either antimiR-451 or mismatch antimiR. These cells were allowed to spontaneously differentiate for 10 days at which time erythrocyte differentiation was analyzed by flow cytometry. Cells were stained for the erythrocyte markers CD71 and Ter119. The most differentiated erythrocytes are in Region 4 (R4) whereas the less differentiated erythroid cells are in Region 2 (R2). The percent gated in each region is listed within the respective gate. It is clear that nucleofection of these cells with antimiR-451 reduces erythroid differentiation when compared to mismatch antimiR nucleofected cells.

The most differentiated erythrocytes are in Region 4 (R4), whereas the less differentiated erythroid cells are in Region 2 (R2) (see FIG. 13). The percent gated in each region is listed within the respective gate in FIG. 13. Interestingly, cells nucleofected with antimiR-451 displayed attenuated erythroid maturation when compared to mismatch nucleofected cells (FIG. 13). These data suggest that inhibition of miR-451 with antimiR-451 results in a disruption of human erythrocyte maturation similar to that seen in miR-451 mutant mice.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for treating polycythemia in a mammalian subject in need thereof comprising administering an inhibitor of miR-451 to the subject, thereby treating polycythemia in the subject.

2. The method of claim 1, wherein the subject's red blood cell count is reduced following administration of the inhibitor of miR-451.

3. The method of claim 1, wherein the inhibitor of miR-451 is an antisense oligonucleotide, and wherein the antisense oligonucleotide is about 8 to about 30 nucleotides in length and comprises a sequence that is at least partially complementary to a mature miR-451 sequence.

4. The method of claim 3, wherein the antisense oligonucleotide comprises a sequence that is at least partially complementary to a sequence of SEQ ID NO: 3.

5. The method of claim 3, wherein the antisense oligonucleotide comprises at least one sugar and/or backbone modification.

6. The method of claim 5, wherein the sugar modification is a 2'-O-methyl modification or a locked nucleic acid modification, and wherein the backbone modification is a phosphorothioate modification.

7. The method of claim 3, wherein the antisense oligonucleotide has a sequence selected from the group consisting of SEQ ID NO: 4, SEQ ID NO: 6, SEQ ID NO: 7, SEQ ID NO: 8, SEQ ID NO: 9, SEQ ID NO: 10, SEQ ID NO: 16, SEQ ID NO: 17, SEQ ID NO: 18, SEQ ID NO: 19, and SEQ ID NO: 20.

8. The method of claim 1, wherein the subject is diagnosed with, suffering from, or at risk of developing polycythemia vera, primary familial and congenital polycythemia, or a disease associated with polycythemia.

9. The method of claim 8, wherein the disease associated with polycythemia is emphysema, chronic obstructive pulmonary disease (COPD), congestive heart failure, sleep apnea, multiple myeloma, or pulmonary hypertension.

* * * * *

SEQUENCE LISTING

<160> NUMBER OF SEQ ID NOS: 22

<210> SEQ ID NO 1
<211> LENGTH: 72
<212> TYPE: RNA
<213> ORGANISM: Homo sapiens

<400> SEQUENCE: 1
cuugggaaug gcaaggaaac cguuaccauu acugaguuua guaaugguaa ugguucucuu      60
gcuauaccca ga                                                          72

<210> SEQ ID NO 2
<211> LENGTH: 72
<212> TYPE: RNA
<213> ORGANISM: Mus musculus

<400> SEQUENCE: 2
cuugggaaug gcgaggaaac cguuaccauu acugaguuua guaaugguaa cgguucucuu      60
gcugcuccca ca                                                          72

<210> SEQ ID NO 3

```
<211> LENGTH: 22
<212> TYPE: RNA
<213> ORGANISM: Homo sapiens

<400> SEQUENCE: 3
aaaccguuac cauuacugag uu                                              22

<210> SEQ ID NO 4
<211> LENGTH: 22
<212> TYPE: RNA
<213> ORGANISM: Artificial Sequence
<220> FEATURE:
<223> OTHER INFORMATION: antimiR-451 oligonucleotide

<400> SEQUENCE: 4
aacucaguaa ugguaacggu uu                                              22

<210> SEQ ID NO 5
<211> LENGTH: 20
<212> TYPE: RNA
<213> ORGANISM: Artificial Sequence
<220> FEATURE:
<223> OTHER INFORMATION: Mismatch control oligonucleotide

<400> SEQUENCE: 5
aacaguaaug guaacgguuu                                                 20

<210> SEQ ID NO 6
<211> LENGTH: 8
<212> TYPE: RNA
<213> ORGANISM: Artificial Sequence
<220> FEATURE:
<223> OTHER INFORMATION: antimiR-451 oligonucleotide

<400> SEQUENCE: 6 aacgguuu                                                               8

<210> SEQ ID NO 7
<211> LENGTH: 10
<212> TYPE: RNA
<213> ORGANISM: Artificial Sequence
<220> FEATURE:
<223> OTHER INFORMATION: antimiR-451 oligonucleotide

<400> SEQUENCE: 7
guaacgguuu                                                            10

<210> SEQ ID NO 8
<211> LENGTH: 12
<212> TYPE: RNA
<213> ORGANISM: Artificial Sequence
<220> FEATURE:
<223> OTHER INFORMATION: antimiR-451 oligonucleotide

<400> SEQUENCE: 8
ugguaacggu uu                                                         12

<210> SEQ ID NO 9
<211> LENGTH: 14
<212> TYPE: RNA
<213> ORGANISM: Artificial Sequence
<220> FEATURE:
<223> OTHER INFORMATION: antimiR-451 oligonucleotide

<400> SEQUENCE: 9
aaugguaacg guuu                                                       14
```

<210> SEQ ID NO 10
<211> LENGTH: 16
<212> TYPE: RNA
<213> ORGANISM: Artificial Sequence
<220> FEATURE:
<223> OTHER INFORMATION: antimiR-451 oligonucleotide

<400> SEQUENCE: 10 guaauggucaa cgguuu                                                         16

<210> SEQ ID NO 11
<211> LENGTH: 23
<212> TYPE: RNA
<213> ORGANISM: Mus musculus

<400> SEQUENCE: 11
ucugguaagg gcagaaacgg uuc                                                  23

<210> SEQ ID NO 12
<211> LENGTH: 24
<212> TYPE: RNA
<213> ORGANISM: Homo sapiens

<400> SEQUENCE: 12
ucuggauaag ggcagaaacg guuc                                                 24

<210> SEQ ID NO 13
<211> LENGTH: 24
<212> TYPE: RNA
<213> ORGANISM: Didelphis sp.

<400> SEQUENCE: 13
ucuggagaag ggcagaaacg guuc                                                 24

<210> SEQ ID NO 14
<211> LENGTH: 26
<212> TYPE: RNA
<213> ORGANISM: Gallus gallus

<400> SEQUENCE: 14
ucuagagaag gacagagaaa cgguuc                                               26

<210> SEQ ID NO 15
<211> LENGTH: 773
<212> TYPE: DNA
<213> ORGANISM: Mus musculus

<400> SEQUENCE: 15
caggctctcc ctgtgcagag gattccctgg acgaggctcc agctccactc cagctccagg           60
taagcagtcc ttggagtggc tgtcagcctg cttataggtc tgcccagagg gaagctcctg          120
cctcacaact tcgtttctgc ctgtaactct ggatccctaa gagacccgag tagaccttag          180
cttccttctc taagccacct ggggttatcc tggaccacag gatcagggag atgctgctct          240
gggagggaag tggaggagca gaggtaggga cttaggtgtc cctgactgac cctgagccaa          300 tccctggct cactccaggc ctgctgctca cctcctcctc caggaccttg ctgggatat            360 catcatatac tgtaagtttg tgatgagaca ctacagtata gatgatgtac tagtctgggt          420
accccacctc cagagcctgc ctggtttgca gcagagatgc agaagtacac gggctcactg          480
ctcggcctaa tcaagcctgc tgacagctgt ggcacttggg aatggcgagg aaaccgttac          540

| | |
|---|---|
| cattactgag tttagtaatg gtaacggttc tcttgctgct cccacaaact gtgccaagaa | 600 |
| gagctcatga ccctggagca gactgctgga agaaaaggac acccaggctg acaagagaat | 660 |
| ggggttgggg gaaagggtac attttcctct tcactgtgcc aaagaaataa aagataagaa | 720 |
| taagagcact tgtcatttaa ctttattagc atccgaggct gggtggttgg atg | 773 |

<210> SEQ ID NO 16
<211> LENGTH: 16
<212> TYPE: RNA
<213> ORGANISM: Artificial Sequence
<220> FEATURE:
<223> OTHER INFORMATION: antimiR-451 oligonucleotide

<400> SEQUENCE: 16
aguaauggua acgguu                                                    16

<210> SEQ ID NO 17
<211> LENGTH: 15
<212> TYPE: RNA
<213> ORGANISM: Artificial Sequence
<220> FEATURE:
<223> OTHER INFORMATION: antimiR-451 oligonucleotide

<400> SEQUENCE: 17
guaaugguaa cgguu                                                     15

<210> SEQ ID NO 18
<211> LENGTH: 15
<212> TYPE: RNA
<213> ORGANISM: Artificial Sequence
<220> FEATURE:
<223> OTHER INFORMATION: antimiR-451 oligonucleotide

<400> SEQUENCE: 18
uaaugguaac gguuu                                                   15

<210> SEQ ID NO 19
<211> LENGTH: 14
<212> TYPE: RNA
<213> ORGANISM: Artificial Sequence
<220> FEATURE:
<223> OTHER INFORMATION: antimiR-451 oligonucleotide

<400> SEQUENCE: 19
uaaugguaac gguu                                                    14

<210> SEQ ID NO 20
<211> LENGTH: 8
<212> TYPE: RNA
<213> ORGANISM: Artificial Sequence
<220> FEATURE:
<223> OTHER INFORMATION: antimiR-451 oligonucleotide

<400> SEQUENCE: 20 uaacgguu                                                               8

<210> SEQ ID NO 21
<211> LENGTH: 16
<212> TYPE: DNA
<213> ORGANISM: Artificial Sequence
<220> FEATURE:
<223> OTHER INFORMATION: antimiR-451 oligonucleotide

<400> SEQUENCE: 21
agtaatggta acggtt                                                  16

```
<210> SEQ ID NO 22
<211> LENGTH: 16
<212> TYPE: DNA
<213> ORGANISM: Artificial Sequence
<220> FEATURE:
<223> OTHER INFORMATION: C. elegans antimiR oligonucleotide

<400> SEQUENCE: 22
tcctagaaag agtaga                                                    16
```